United States Patent [19]
Degelmann et al.

[11] Patent Number: 6,103,894
[45] Date of Patent: *Aug. 15, 2000

[54] PROCESS FOR THE HYDROGENATION OF SUGARS

[75] Inventors: Hanspeter Degelmann, Worms; Jörg Kowalczyk, Bockenheim; Markwart Kunz; Matthias Schüttenhelm, both of Worms, all of Germany

[73] Assignee: Sudzucker Aktiengesellschaft, Mannheim, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/004,801

[22] Filed: Jan. 9, 1998

Related U.S. Application Data

[63] Continuation of application No. 09/004,801, Jan. 9, 1998.

[30] Foreign Application Priority Data

Jan. 17, 1997 [DE] Germany ............................ 197 01 439

[51] Int. Cl.⁷ ................................ C07H 1/00; C07H 3/04
[52] U.S. Cl. ..................................... 536/124; 536/123.13
[58] Field of Search .................................. 536/18.5, 124, 536/123.13; 568/863, 852

[56] References Cited

U.S. PATENT DOCUMENTS

| | | | |
|---|---|---|---|
| 3,965,199 | 6/1976 | Wright | 260/635 C |
| 4,117,173 | 9/1978 | Schwieck et al. | 426/548 |
| 4,684,720 | 8/1987 | Darsow et al. | 536/124 |
| 4,795,733 | 1/1989 | De Thomas | 502/327 |
| 5,162,517 | 11/1992 | Darsow | 536/124 |
| 5,644,044 | 7/1997 | Darsow | 536/18.6 |
| 5,679,781 | 10/1997 | Goldscher | 536/18.5 |

FOREIGN PATENT DOCUMENTS 195 23 008   1/1996   Germany ...................... C07H 15/04

OTHER PUBLICATIONS

Schiweck, H. "Palatinit®—Technological Properties" from *Proc. ERGOB Conf., (Geneva 1978)*, pp. 138–144, 1978.

*Primary Examiner*—Howard C. Lee
*Attorney, Agent, or Firm*—Darby & Darby

[57] ABSTRACT

The invention relates to a process for the hydrogenation of sugars and sugar mixtures from the group consisting of isomaltulose, trehalulose, maltulose, leucrose and lactulose to sugar alcohols or sugar alcohol mixtures wherein the sugars or sugar mixtures are hydrogenated with hydrogen in an aqueous solution at elevated temperature and elevated pressure, using a nickel-containing catalyst attached to a carrier.

18 Claims, 2 Drawing Sheets

PROCESS FOR THE HYDROGENATION OF SUGARS

This is a continuation of application Ser. No. 09/004,801, filed Jan. 9, 1998. The most recent of these prior applications is hereby incorporated herein by reference, in its entirety.

BACKGROUND OF THE INVENTION

1. Field of the Invention

The present invention relates to a process for the hydrogenation of sugars and sugar mixtures from the group consisting of isomaltulose, trehalulose, maltulose, leucrose and lactulose to the corresponding sugar alcohols or sugar alcohol mixtures wherein the sugars or sugar mixtures are hydrogenated with hydrogen in an aqueous solution at elevated temperature and elevated pressure, using a nickel-containing catalyst attached to a carrier.

2. Description of the Related Art

EP 0 152 779 B1 describes a process for manufacturing a mixture of 1-0-α-D-glocupyranosil-D-mannite (hereafter called 1,1-GPM) and 6-0-α-D-glocupyranosil-D-sorbite (hereafter called 1,6-GPS) from 6-0-α-D-glocupyranosil-D-fructose (isomaltulose, palatinose$^R$). In the described process, isomaltulose is hydrogenated continuously at elevated pressure and elevated temperature in a fixed-bed process using carrier-free catalysts taken from the eighth subgroup of the periodic system, in particular nickel, cobalt and iron. The process described above produces 1,6-GPS and 1,1-GPM with a ratio of approximately 1:1.

Another process for producing 1,6-GPS and 1,1-GPM from isomaltulose is known from DE 44 16 115 A1. Here, the catalyst which was described in EP 0 152 779 B1, contains additional elements from the sixth subgroup of the periodic system. This process also produces 1,6-GPS and 1,1-GPM with a ratio of about 1:1. DE 44 16 408 A1 and DE 39 34 457 A1 also describe processes for the hydrogenation of sugars, such as glucose, xylose, lactulose or maltose. The catalysts used in the hydrogenation reaction are carrier-free formed bodies made from elements of the eighth and sixth subgroup of the periodic system.

If stereo-isomers (epimers) can be formed by hydrogenating an educt, such as isomaltulose, then it is possible to adjust the stereo-selectivity of the reaction such that the reaction products are formed with a predetermined ratio. It is therefore desirable to develop a process for certain applications which produces reaction products with a predetermined ratio which could hitherto not be attained. It is also desirable to improve the process flow, the handling of the catalysts and the process costs of the conventional processes.

SUMMARY OF THE INVENTION

The present invention advantageously provides a process for the hydrogenation of sugars from the group consisting of isomaltulose, leucrose, trehalulose, maltulose and lactulose to sugar alcohols which overcomes the aforedescribed disadvantages; moreover, the products produced with the invention have a composition which was unattainable with conventional processes.

The present invention solves the technical problem by providing a process according to the independent claim. In particular, a process is provided for hydrogenating a sugar to a sugar alcohol, wherein the sugar is contacted with hydrogen in an aqueous solution at elevated temperature and at an elevated pressure in the presence of a catalyst attached to a carrier. In preferred embodiments, the sugar comprises isomaltulose, leucrose, trehalulose, lactulose, maltulose, or mixtures of any of the foregoing. The active component of the catalyst includes nickel, and may additional comprise nickel oxide and/or tungsten oxide. Catalysts of this type are known from U.S. Pat. No. 3,965,199 to which reference is made with respect to the composition and the preparation of the catalyst used in the present invention, and which is incorporated herein by reference. Most preferably, the catalyst is in a commercially available extruded form.

In the present invention, a nickel-containing catalyst attached to a carrier refers to a catalyst with an active component which is not prepared by alkaline activation of aluminum alloys with other metals and which does not contain aluminum alloys, not even as residues. The catalyst of the invention is therefore not a Raney nickel catalyst.

Most advantageously, the composition of the product produced with the process of the invention is different from conventional processes, in particular in situations where different stereo-isomers are produced from an educt a hydrogenation reaction.

In another preferred embodiment, isomaltulose is hydrogenated. The composition of the reaction product here has a different composition than is expected from a conventional process, where about 50 wt.-% 1,1-GPM and 50 wt.-% 1,6-GPS are generated. The reaction product has a larger 1,1-GPM fraction and a smaller 1,6-GPS fraction. Advantageously, the process of the invention can also be used for hydrogenating trehalulose to 1,1-GPM and 1-0-α-D-glocupyranosil-D-sorbite (1,1-GPS), lactulose to lactite and 3-0-β-D-glucopyranosil-D-mannite, maltulose to 3-0-α-D-glucopyranosil-D-mannite and 4-0-α-D-glucopyranosil-D-sorbite (maltite), and leucrose to 5-0-α-D-glucopyranosil-D-sorbite (1,5-GPS) and 2-0-α-D-glocupyranosil-D-mannite (1,2-GPM). Advantageously, the product has a relatively higher 1,1-GPM fraction in the case of trehalulose, a relatively higher 3-0-α-D-glucopyranosil-D-mannite fraction in the case of maltulose, and a relatively higher 3-0-β-D-glucopyranosil-D-mannite fraction in the case of lactulose. When the aforedescribed glucopyranosil-substituted ketoses are hydrogenated, the invention thus produces an larger mannite epimer fraction and a smaller sorbite epimer fraction in the product.

Those sugar alcohol stereo isomers are referred to as mannite and sorbite epimers which are produced during hydrogenation of the prochiral carbonyl carbon atom of the ketose or the glucopyranosil-substituted fructose (isomaltulose, trehalulose, etc.). A mannite epimer of the present invention is an epimer which has the polyol chain of the glucopyranosil-substituted D-mannose. A sorbite epimer of the present invention is an epimer which has the polyol chain of the glucopyranosil-substituted D-glucose.

In another preferred embodiment, sugar mixtures, such as the mixture of isomaltulose and trehalulose described in EP 0 625 578 B1, as well as glucose, fructose, isomelezitose, residual saccharose, isomaltose and oligosaccharides are hydrogenated as well. The product of the invention also contains a larger mannite epimer fraction.

In still another preferred embodiment, the catalyst used with the invention consists of 5–50 wt.-% nickel or nickel oxide and 0.5–16 wt.-% tungsten oxide, relative to the total weight of the catalyst, including the carrier material.

In yet another preferred embodiment, the catalyst has a density of between about 0.60 to about 0.70 kg/l.

The catalyst of the invention is attached to a carrier. The carrier can be, for example, silicon dioxide, diatomaceous earth, $TiO_2$, $SiO_2 \ast Al_2O_3$, clay, zeolite, $ZrO_2$, silicate or aluminum oxide ($Al_2O_3$), or mixtures of any of the foregoing.

Aside from nickel, nickel oxide and tungsten oxide, in particular tungsten trioxide, the catalysts used with the present invention can also contain up to 20 wt. - %, preferably 15 wt.-% (referenced to a carrier-free formed body) of other metals. These other metals do not have to be active catalysts and can be comprised of, for example, iron, manganese, titanium, aluminum or silicon.

The catalysts used with the present invention are prepared from solution by sedimentation and adsorption, respectively, of the active components of the catalysts, i.e. nickel and possible nickel oxide and/or tungsten oxide, onto the inert carrier material. The catalyst-precursor prepared in this manner is readily useable in the hydrogenation process immediately after activation with hydrogen. According to the invention, the catalyst-precursor can also be processed further, preferably by an extrusion process. Moreover, the catalyst-precursor in the present invention is manufactured by pressing the impregnated carrier material described above under high pressure, if necessary, with the addition of graphite and/or adhesive in quantities of less than 1 wt.-%, referenced to the weight of the catalyst, to improve the adhesion of the particles. The formed bodies are subsequently calcined and reduced with hydrogen; the active metallic catalytic crystallites are formed during the last step. In stabilized form, the surface of the catalyst has an inert adsorption layer which is activated only after exposure to hydrogen; hydrogen removes the monomolecular adsorption layer or reduces the oxide layer, as the case may be, thereby activating the catalyst.

The catalysts can have the form of spheres, tablets, granulates, rods, with or without bores. The catalysts can, of course, also be in powder form, if the catalysts are used, for example, in a suspension process.

The educt used in the process of the invention is lactulose, trehalulose, maltulose, isomaltulose, leucrose or mixtures thereof. The sugars can be in liquid form. According to a particularly preferred embodiment of the invention, the educt is dissolved in demineralized water, with the solution adjusted to about 10 to about 70 wt.-%, preferably about 15 to about 50 wt.-%, most preferably about 40 wt.-% (referenced to dry solid). The pH value is preferably between 3.0 and 12.0. The pH value can be adjusted, for example, by adding water-soluble basic compounds, such as alkali carbonates or ammonia in aqueous solution, or by adding acidic compounds, such as saccharic acids, sorbic acid or citric acid.

In the process of the invention, pure hydrogen which is precompressed to about 50 to about 450 bar, preferably to about 150 to about 300 bar, is used for hydrogenation. Preferably, the hydrogenation can be carried out continuously in a fixed-bed process, using a conventional parallel flow or a counterflow process. According to the invention, however, the hydrogenation can also be carried out discontinuously with a suspension process, using the powder catalyst or a pulverized fixed-bed catalyst.

The process of the invention is preferably carried out in a hydrogenation reactor in the form of a high-pressure steel tube, wherein the hydrogenation reactor is filled either partially or entirely with the catalyst attached to a carrier. The catalyst can also be placed in a catalyst basket. It is understood by those skilled in the art that the invention also includes the use of hydrogenation reactors which are constructed, for example, from a various individual reactors. In a particularly preferred embodiment of the invention, the hydrogenation reactor includes stirrers for the purpose of bringing the educts and the hydrogenation gas into closer contact with each other.

The hydrogenation is preferably carried out at temperatures between about 60° C. and about 150° C., preferably between about 70° C. and about 120° C.

With the process of the invention, sugar alcohols or sugar alcohol mixtures with a purity of better than 99 wt.-% can be obtained, referenced to the dry solid. The fraction of unreacted sugars or sugar mixtures can be reduced to 0.2 wt.-% or less.

Other objects and features of the present invention will become apparent from the following detailed description considered in conjunction with the accompanying drawings. It is to be understood, however, that the drawings are intended solely for purposes of illustration and not as a definition of the limits of the invention, for which reference should be made to the appended claims.

BRIEF DESCRIPTION OF THE DRAWINGS

The invention will now be described in greater detail with reference to the appended drawing and the related examples. In the drawing is shown in.

EXAMPLES AND DETAILED DESCRIPTION OF THE PRESENTLY PREFERRED EMBODIMENTS

EXAMPLE 1

Hydrogenation of isomaltulose with the process of the invention:

Isomaltulose was hydrogenated in a hydrogenation reactor 2 with an inner volume of 750 ml using the discontinuous fixed-bed process. A catalyst basket 4 (volume: 138.9 cm$^3$) with an inner volume of 138.9 cm$^3$ is located inside a stainless steel tube in the hydrogenation reactor 2. The catalyst basket 4 contains 146.77 g (wet) or 70.27 (dry) nickel, nickel oxide and tungsten oxide catalyst (Südchemie T-4190 RS 3 mm).

Preferably, the active catalytic material (nickel, nickel oxide, tungsten oxide) is first precipitated from a soluble form and then adsorbed on the finely dispersed carrier material (carrier: aluminum silicate). The resulting material is subsequently mixed with binders, pore forming materials and other components, whereafter the homogeneous mixture is extruded into formed bodies, then dried and calcined. The mixture can also contain lubricants, pore forming materials, resilient additives, plastifiers, etc., which are added to promote pore formation. The formed bodies are, if necessary, dried between 80° C. and 120° C. and subsequently calcined at temperatures below 850° C., preferably between 500° C. and 700° C. The extruded material hardens during the calcination step and the macropore and mesopore system develops. In a subsequent activation step, the oxide compounds are reduced on the carrier surface (nickel oxide, tungsten oxide) with hydrogen at temperatures between 300° C. and 600° C. The surface of the catalyst is rendered inert (stabilized) by treating the surface with $O_2$/CO mixtures so that the catalyst can then be stored in air. The active area is hereby covered with a thin monomolecular adsorption layer.

Figure 1:
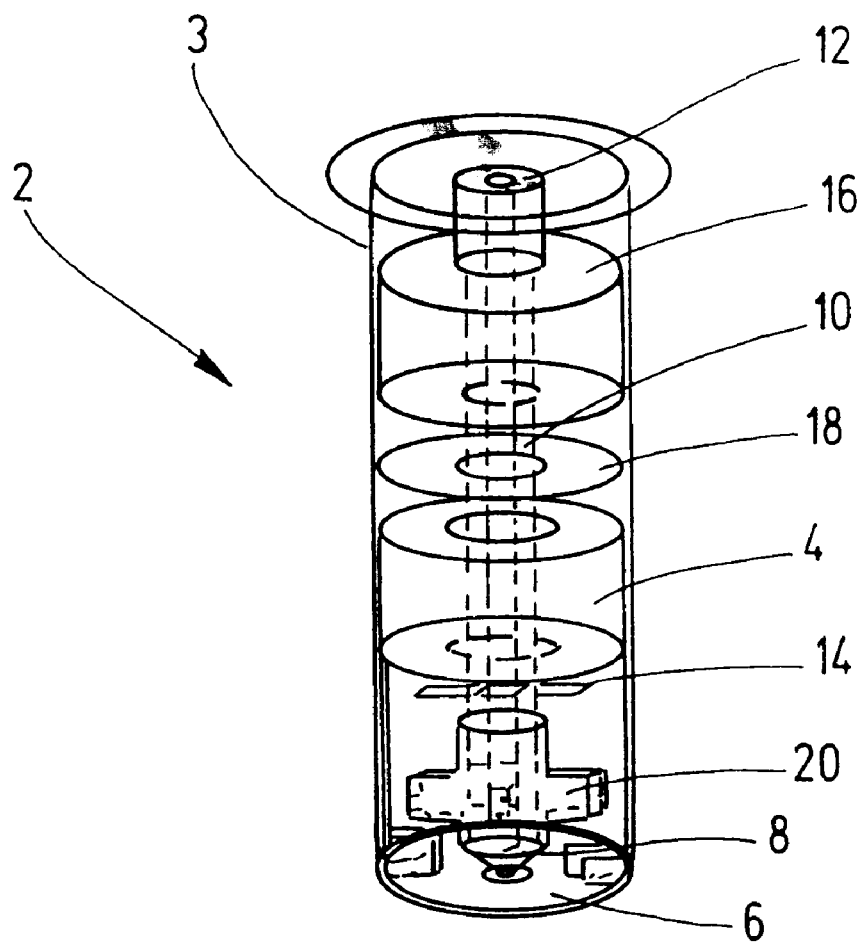
FIG. 1 is a schematic illustration of a hydrogenation reactor used in accordance with the invention.

The centering disc 6 of the hydrogenation reactor 2 which is located near the bottom of the reactor 2, includes a lower shaft bearing 8. The lower shaft bearing 8 and the upper shaft bearing 12 support a stainless steel stirrer shaft 10 which carries stirring paddles 14. The stirrer shaft 10 is driven electro-magnetically by the stirrer magnet 16. In FIG. 1, there are also illustrated flow interrupters 18 and a gas distribution paddle 20.

500 ml aqueous educt solution, in the present example isomaltulose solution (0.1% fructose, 0.1% glucose, 98% isomaltulose, 1.2% trehalulose, 0.3% isomaltose, 0.3% residue, all numbers are given in wt.-%) (30 wt.-% solid material) (pH: 5.3), are introduced into the hydrogenation reactor 2. Hydrogen under a pressure of 150 bar is introduced through the gas distribution paddle 20, while the stirrer 10 rotates at 600 RPM and a temperature of 70° C. is maintained. Samples from the reagent solution (pH: 6.5) are withdrawn at the beginning of the reaction and after 2, 3, 4, 5, 6 and 22 hours and tested for isomaltulose, 1,1-GPM, 1,6-GPS, mannite, sorbite and saccharite residue.

Figure 2:
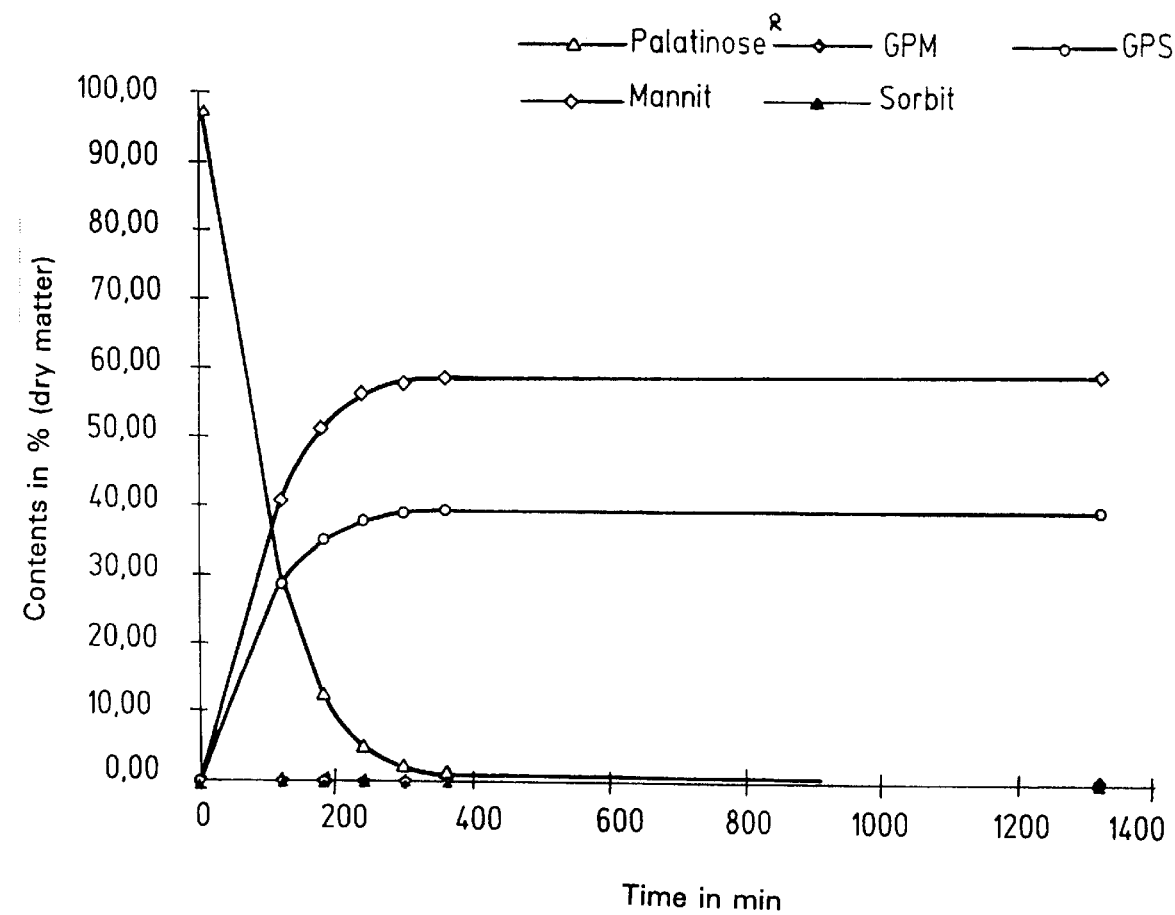
FIG. 2 a graphic representation of the product formation according to FIG. 1 as a function of time.

The results are shown in Table 1 and graphed in FIG. 2.

TABLE 1

| Duration of the experiment in min. | isomaltulose % | 1,1-GPM | 1,6-GPS | Mannite | Sorbite | Residue |
|---|---|---|---|---|---|---|
| 0 | 98.00 | 0.00 | 0.00 | 0.00 | 0.00 | 2.00 |
| 120 | 29.49 | 40.96 | 28.65 | 0.03 | 0.03 | 0.84 |
| 180 | 12.56 | 51.60 | 35.22 | 0.03 | 0.05 | 0.54 |
| 240 | 4.64 | 56.53 | 38.12 | 0.04 | 0.05 | 0.62 |
| 300 | 1.93 | 58.20 | 39.20 | 0.05 | 0.07 | 0.55 |
| 360 | 1.02 | 58.81 | 39.52 | 0.05 | 0.06 | 0.54 |
| 1320 | 0.11 | 59.45 | 39.92 | 0.05 | 0.08 | 0.39 |

Hydrogenation with the process of the invention produces a product with a composition which is different from the expected 50:50 ratio of 1,1-GPM to 1,6-GPS. Comparatively more mannite epimer and less sorbite epimer is produced.

EXAMPLE 2

Hydrogenation of isomaltulose with the process of the invention:

The conditions and the apparatus for the process are identical to those described in Example 1. However, only one sample was drawn after 22 hours. The educt used here has the composition shown in Table 2 (in the following, % values are given in wt.-%, unless indicated otherwise):

TABLE 2

| No. | Educt | Contents |
|---|---|---|
| 1 | Isomaltulose | 98.50% as dry solid |
| 2 | Trehalulose | 1.13% as dry solid |
| 3 | Isomaltose | 0.23% as dry solid |
| 4 | Isomelezitose | 0.08% as dry solid |
| 5 | Saccharide residue | 0.06% as dry solid |

It is evident from Table 3 that the product produced with the process of the invention has a different composition than products obtained with an otherwise identical process which uses a reference catalyst. The reference process employed a carrier-free Raney nickel catalyst which was prepared by compressing activated nickel powder into tablets. The tablets are cylindrical with a height of 5 mm and a diameter of 5 mm and have a crush strength of 147 N and an interior surface of 33 m²/g.

TABLE 3

| No. | Product | Reference process | Invention |
|---|---|---|---|
| 1 | 1,1-GPM | 49.09% as dry solid | 58.34% as dry solid |
| 2 | 1,6-GPS | 49.45% as dry solid | 40.83% as dry solid |
| 3 | GPI | 0.33% as dry solid | 0.07% as dry solid |
| 4 | Mannite | 0.05% as dry solid | 0.05% as dry solid |
| 5 | Sorbite | 0.11% as dry solid | 0.09% as dry solid |
| 6 | hydrogenated and unhydrogenated saccharide residues | 0.97% as dry solid | 0.61 % as dry solid |

The reference process produces 1,1-GPM and 1,6-GPS in a 1:1 ratio, whereas the process of the invention produces a greater 1,1-GPM fraction and a smaller 1,6-GPS fraction in the product.

EXAMPLE 3

Hydrogenation of a mixture of isomaltulose and trehalulose (known from EP 0 625 578 B1):

The conditions and the apparatus for the process are identical to those described in Example 1. The reference method uses a catalyst identical to the catalyst of Example 2.

The educt in this example is a sugar mixture with the composition shown in Table 4:

TABLE 4

| No. | Educt | Contents |
|---|---|---|
| 1 | Glucose | 3.64% as dry solid |
| 2 | Fructose | 2.50% as dry solid |
| 3 | Isomaltulose | 84.02% as dry solid |
| 4 | Trehalulose | 7.64% as dry solid |
| 5 | Isomaltose | 1.39% as dry solid |
| 6 | Isomelezitose | 0.38% as dry solid |
| 7 | Saccharide residue | 0.43% as dry solid |

Hydrogenation with the process of the invention and with the reference process gives the following result:

TABLE 5

| No. | Product | Reference process | Invention |
|---|---|---|---|
| 1 | 1,1-GPM | 46.51% as dry solid | 54.57 as dry solid |
| 2 | 1,6-GPS + 1,1-GPS | 46.47% as dry solid | 38.29% as dry solid |
| 3 | Mannite | 1.59% as dry solid | 1.22% as dry solid |
| 4 | Sorbite | 3.78% as dry solid | 3.70% as dry solid |
| 5 | hydrogenated and unhydrogenated saccharide residues | 1.65% as dry solid | 2.01% as dry solid |

The reference process produces 1,1-GPM and 1.1-GPS/ 1,6-GPS with a ratio of about 1:1, whereas the process of the invention produces a greater 1,1-GPM fraction and a smaller 1.1-GPS/1,6-GPS fraction in the product.

EXAMPLE 4

Hydrogenation of lactulose with the process of the invention:

The process flow and the apparatus for the process are identical to those described in Example 1. The reference method uses a catalyst identical to the catalyst of Example 2.

Hydrogenation of lactulose (99.48 wt.-%, 0.52 wt.-% saccharide residue, referenced to dry solid) with the process of the invention and with a conventional process gives the following result:

TABLE 6

| No. | Product | Reference process | Invention |
|---|---|---|---|
| 1 | 1,3-GalPM | 46.38% as dry solid | 64.29% as dry solid |
| 2 | 1,4-GalPS (Lactite) | 51.60% as dry solid | 34.73% as dry solid |
| 3 | Mannite | 0.38% as dry solid | 0.08% as dry solid |
| 4 | Sorbite | 0.04% as dry solid | 0.09% as dry solid |
| 5 | Galactite | 0.91% as dry solid | 0.64% as dry solid |
| 6 | hydrogenated and unhydrogenated saccharide residues | 0.69% as dry solid | 0.17% as dry solid |

The process of the invention produces a comparatively greater 1,3-GalPM fraction and a comparatively smaller 1,4-GalPS (Lactite) fraction in the product.

EXAMPLE 5

Hydrogenation of trehalulose:

The process flow and the apparatus for the process are identical to those described in Example 1. The reference method uses a catalyst identical to the catalyst of Example 2.

Hydrogenation of trehalulose (94.82 wt.-%, 2.50% isomaltulose, 2.68% saccharide residue, wt.-% referenced to dry solid) with the process of the invention and with a conventional process gives the following result:

TABLE 7

| No. | Product | Reference process | Invention |
|---|---|---|---|
| 1 | 1,1-GPM | 53.29% as dry solid | 78.95% as dry solid |
| 2 | 1,1-GPS + 1,6-GPS | 41.10% as dry solid | 15.46% as dry solid |
| 3 | Mannite | 0.02% as dry solid | 0.39% as dry solid |
| 4 | Sorbite | 1.02% as dry solid | 1.47% as dry solid |
| 5 | hydrogenated and unhydrogenated saccharide residues | 4.57% as dry solid | 3.73% as dry solid |

The process of the invention produces a significantly larger 1,1-GPM fraction in the product than the conventional process. The 1,1-GPS fraction is reduced accordingly. The 1,6-GPS is produced by the isomaltulose residues contained in the educt.

EXAMPLE 6

Hydrogenation of maltulose:

The process flow and the apparatus for the process are identical to those described in Example 1. The reference method uses a catalyst identical to the catalyst of Example 2.

The composition of the educt was as follows:

TABLE 8

| No. | Educt | Contents |
|---|---|---|
| 1 | Maltulose | 83.43% as dry solid |
| 2 | Fructose | 5.74% as dry solid |
| 3 | Glucose | 3.87% as dry solid |
| 4 | Saccharide residue | 6.96% as dry solid |

Hydrogenation with the process of the invention and with the reference process the following result:

TABLE 9

| No. | Product | Reference process | Invention |
|---|---|---|---|
| 1 | 1,3-GPM | 37.29% as dry solid | 44.78% as dry solid |
| 2 | 1,4-GPS (Maltite) | 41.49% as dry solid | 29.23% as dry. solid |
| 3 | Sorbite | 7.36% as dry solid | 15.15% as dry solid |
| 4 | Mannite | 5.44% as dry solid | 8.02% as dry solid |
| 5 | hydrogenated and unhydrogenated saccharide residues | 7.97% as dry solid | 2.82% as dry solid |

The process of the invention produces comparatively more mannite epimers than sorbite epimers in the product.

EXAMPLE 7

Hydrogenation of sugars with powder catalysts (slurry process, discontinuous process):

(1) Autoclave system and experimental parameters:

750 ml laboratory autoclave with inductively operated stirrer

Reaction temperature: 70° C.

Hydrogen pressure: 150 bar

Stirrer RPM: 600 rpm

Sugar solution: 500 ml with 30% dry solid

Catalyst quantity: ca. 25 g (wet)

Reaction time: 22 h (2) Assay:

The reaction solution (500 ml, 30% dry solid) is introduced into the temperature-stabilized autoclave of FIG. 1; however, the basket is omitted and the stirrer is modified. Subsequently, 25 g powdered catalyst (the catalyst has the same composition as in Example 1) is added, whereafter (not before) the stirrer shaft is inserted. The system is then rendered inert by purging 3 times with nitrogen, whereafter hydrogenation is carried out at 150 bar and a reaction temperature of 70° C. After 22 hours, the system is cooled down to room temperature and depressurized. After the system is purged with nitrogen, the product solution is withdrawn and the catalyst filtered out.

EXAMPLE 8

Hydrogenation of isomaltulose with a powder catalyst:

The process flow and the apparatus for the process are identical to those described in Example 7. The educt has the following composition:

TABLE 10

| No. | Educt | Contents |
|---|---|---|
| 1 | Fructose | 0.15% as dry solid |
| 2 | Glucose | 0.12% as dry solid |
| 3 | Isomaltulose | 98.21% as dry solid |
| 4 | Trehalulose | 1.30% as dry solid |
| 5 | Isomaltose | 0.10% as dry solid |
| 6 | Residue | 0.12% as dry solid |

The hydrogenation according to the present invention gives the following result:

TABLE 11

| No. | Product | Invention |
|---|---|---|
| 1 | 1,1-GPM | 52.29% as dry solid |
| 2 | 1,6-GPS | 46.74% as dry solid |

TABLE 11-continued

| No. | Product | Invention |
| --- | --- | --- |
| 3 | Mannite | 0.07% as dry solid |
| 4 | Sorbite | 0.13% as dry solid |
| 5 | hydrogenated and unhydrogenated saccharide residues | 0.77% as dry solid |

The product contains more 1,1-GPM and less 1,6-GPS than expected (a 1:1 ratio of 1,1-GPM to 1,6-GPS was expected).

EXAMPLE 9

Hydrogenation of trehalulose with a powder catalyst:

The process flow and the apparatus for the process are identical to those described in Example 7. The educt has the following composition:

TABLE 12

| No. | Educt | Contents |
| --- | --- | --- |
| 1 | Fructose | 0.16% as dry solid |
| 2 | Glucose | 2.59% as dry solid |
| 3 | Isomaltulose | 2.61% as dry solid |
| 4 | Trehalulose | 91.80% as dry solid |
| 5 | Saccharide residue | 2.84% as dry solid |

The hydrogenation according to the present invention gives the following result:

TABLE 13

| No. | Product | Invention |
| --- | --- | --- |
| 1 | 1,1-GPM | 60.82% as dry solid |
| 2 | 1,1-GPS + 1,6-GPS | 32.17% as dry solid |
| 3 | Mannite | 0.10% as dry solid |
| 4 | Sorbite | 1.16% as dry solid |
| 5 | hydrogenated and unhydrogenated saccharide residues | 5.75% as dry solid |

The product contains a greater 1,1-GPM fraction and a smaller 1,1-GPS fraction. The 1,6-GPS is produced by the isomaltulose residues contained in the educt.

Thus, while there have been shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A process for the hydrogenation of a sugar selected from the group consisting of isomaltulose, trehalulose, maltulose, leucrose, lactulose and mixtures thereof to a product containing a larger fraction of an epimer which has a polyol chain of a glucopyranosyl-substituted D-mannose and a smaller fraction of an epimer which has a polyol chain of a glucopyranosyl-substituted D-glucose wherein the sugar or the sugar mixture is hydrogenated in aqueous solution at an elevated temperature and a pressure of approximately 50 bar to approximately 450 bar, with hydrogen in the presence of a nickel-containing catalyst attached to a carrier, wherein said catalyst consists essentially of (1) nickel and (2) nickel oxide and (3) tungsten oxide.

2. The process as defined in claim 1, wherein said catalyst has a density of between approximately 0.60 and approximately 0.70 kg/l as referenced to the total weight of the catalyst including the carrier.

3. The process as defined in claim 1 wherein the (1) nickel in said catalyst is from approximately 5 to about 50 wt.-% as referenced to the total weight of the catalyst including the carrier.

4. The process as defined in claim 1 wherein the (1) nickel or (2) nickel oxide in said catalyst is from approximately 5 to approximately 50 wt.-% and the (3) tungsten oxide in said catalyst is from approximately 0.5 to approximately 16 wt.-% and wherein the weight percent of ((1) or (2)) and (3) are referenced to the total weight of the catalyst including the carrier.

5. The process as defined in claim 1, wherein said carrier comprises silicon dioxide and aluminum oxide.

6. The process as defined in claim 1, wherein said catalyst is fabricated by an extrusion process.

7. The process as defined in claim 1, wherein said hydrogenation is continuous, semi-continuous or discontinuous.

8. The process as defined in claim 1, wherein said hydrogenation is carried out with a fixed-bed or with a suspension process.

9. The process as defined in claim 1, wherein said pressure is between approximately 50 and approximately 450 bar.

10. The process as defined in claim 1, wherein said temperature is between approximately 60° C. and approximately 150° C.

11. The process as defined in claim 10, wherein said temperature is approximately 70° C.

12. The process as defined in claim 1 wherein said sugar is present in said solution at a concentration between approximately 10 to approximately 70 wt.-%.

13. The process as defined in claim 12 wherein said sugar concentration is approximately 15 to approximately 50 wt.-%.

14. The process as defined in claim 13, wherein said sugar concentration is approximately 40 wt.-%.

15. The process as defined in claim 1, wherein said sugar or sugar mixture additionally contains glucose or fructose.

16. The process as defined in claim 10, wherein said temperature is between approximately 60° C. and approximately 80° C.

17. The process as defined in claim 9, wherein said pressure is between approximately 200 bar and approximately 450 bar.

18. The process of claim 1 wherein said catalyst further consists essentially of iron, manganese, titanium, silica or aluminum wherein said aluminum is not an aluminum alloy.

* * * * *